(12) United States Patent
Friebe et al.

(10) Patent No.: US 6,307,051 B1
(45) Date of Patent: Oct. 23, 2001

(54) 2-ALKYLIDENE HYDROXYCOUMARANONE DERIVATIVES

(75) Inventors: Walter-Gunar Friebe, Mannheim; Bernhard Koenig, Berg; Hans-Willi Krell; Sabine Woelle, both of Penzberg, all of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/497,220

(22) Filed: Jan. 31, 2000

(30) Foreign Application Priority Data

Jan. 30, 1999 (EP) .................................... 99101956

(51) Int. Cl.[7] ....................... A61K 31/445; C07D 213/02; C07D 405/12

(52) U.S. Cl. ........................... 546/193; 546/197; 514/321

(58) Field of Search .................... 546/193, 197; 514/321

(56) References Cited

U.S. PATENT DOCUMENTS

| | | | |
|---|---|---|---|
| 4,185,110 | * 1/1980 | Eichenberger | 424/275 |
| 4,486,442 | 12/1984 | Friebe et al. | 546/197 |
| 5,886,191 | * 3/1999 | Dominguez | 598/491 |

FOREIGN PATENT DOCUMENTS

| | | |
|---|---|---|
| 088986 | 9/1983 | (EP) . |
| 02-215779 | * 8/1992 | (JP) . |
| 96/12718 | * 2/1996 | (WO) . |

OTHER PUBLICATIONS

Eichenberger et al. "Benzoheterocyclic glyoxylic acid derivatives" CA 89:179847 (1978).*
J. Am. Chem. Soc. vol. 61, pp. 2328–2329 (1939).

* cited by examiner

*Primary Examiner*—Ceila Chang
(74) *Attorney, Agent, or Firm*—George W. Johnston; Patricia S. Rocha-Tramaloni; Robert A. Silverman

(57) ABSTRACT

New compounds of formula I

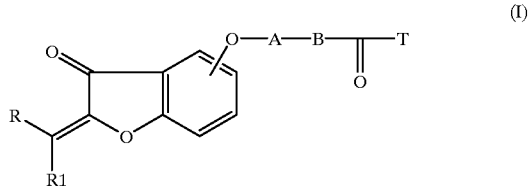

wherein:
R and $R^1$ are independently selected from hydrogen, $(C_1$–$C_6)$alkyl, styryl and $(C_3$–$C_6)$cycloalkyl or, taken together with the carbon to which they are linked, form a $(C_3$–$C_6)$cycloalkyl group;
A is selected from the following groups:

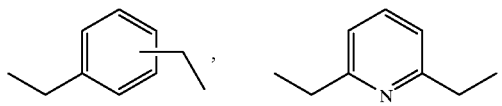

—$CH_2$C≡$CCH_2$—,
or —$(CH_2)_q$—NH—$(CH_2)_q$—,
wherein q is an integer from 2 to 3
B is selected from

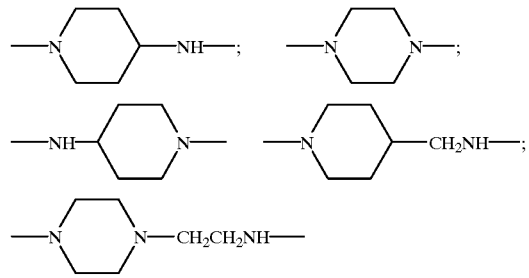

T is selected from —$CH_2$—C≡CH, —C≡CH, —$(CH_2)_p$—$R_3$, —CH=CH—$R_3$, —$CH_2$—NHCO—$R_3$, —$(CH_2)_p$—O—$R_3$, —CH($NH_2$)—$CH_2R_3$, in which p is 0 or an integer from 1 to 4,
$R_3$ is a carbocyclic or heterocyclic ring as medicaments having antitumor and/or antimetastatic activities.

18 Claims, No Drawings

2-ALKYLIDENE HYDROXYCOUMARANONE DERIVATIVES

FIELD OF THE INVENTION

The present invention relates to derivatives of 2-alkylidene hydroxycoumaranones wherein the hydroxy group is substituted by a nitrogen-containing residue. These compounds are uPA-uPAR antagonists and have antitumor and antimetastatic activity.

BACKGROUND OF THE INVENTION

The serine protease uPA (urokinase-type plasminogen activator) catalyzes the activation of plasminogen to plasmin which is involved in a variety of physiological and pathological processes. uPA is a multi-domain protein having a catalytic "B" chain (amino-acids 144–411) and an amino-terminal fragment ("ATF", aa 1–143) comprised of a growth factor-like domain (aa 4–43) and a kringle domain (aa 47–135). uPA is a multifunctional protein involved in tissue proteolysis, cellular migration, cellular proliferation and growth factor activation. uPA is released from cells as a virtually inactive pro-enzyme, pro-uPA. The activation of the single-chain pro-uPA by plasmin (leading to the active two-chain form) is regulated by tight control mechanisms which are not completely understood yet. Most of the uPA activities are confined to the cell surface and the pericellular environment. This is accomplished by binding to a specific, high-affinity receptor on the cell surface (uPAR). Both forms of uPA bind to uPAR with similar affinity. The binding interaction is mediated by the growth factor-like domain [S. A. Rabbani et al., *J. Biol. Chem.*, 267, 14151–56, 1992].

The uPA receptor is a three domain glycoprotein where each triplicated motif comprises a cysteine rich consensus sequence of approximately 90 amino acids [M. Plough et al., *J. Biol. Chem.*, 268, 17539–46, 1993]. uPAR is anchored to the cell membrane by a glycosyl-phosphatidylinositol moiety (GPI anchor). uPAR binds uPA with $K_D$ values between $10^{-10}$ and $10^{-9}$ M, depending on the experimental system. The major determinants for uPA binding are located in the N-terminal domain 1. uPAR can be cleaved by uPA and plasmin, liberating a water soluble domain 1 and by the action of phospholipase C, three domains uPAR (1+2+3) can be released from the cell surface. This latter form of uPAR is also water soluble because the GPI-anchor is missing.

The inhibition of uPA dependent phenomena can principally be approached in two ways, either by direct inhibition of the proteolytic activity or by inhibition of uPA receptor binding. The latter strategy has the potential of achieving greater specificity since inhibition might be localized to the pericellular environment.

A bacteriophage display technique and protein engineering have recently been used to discover peptidic and species-specific uPAR antagonists [Goodson et al., *PNAS*, 91, 7129, 1994; Stratton-Thomas et al., *Prot. Eng.*, 5, 463–470, 1995, respectively].

The uPA/uPAR system has been shown to be implicated in a variety of invasive biological processes such as tumor metastasis, trophoblast implantation, inflammation and angiogenesis. Therefore, uPAR antagonists should be able to block tumor invasiveness, metastasis and angiogenesis. Formulations containing uPAR antagonists represent novel therapeutic treatments for a number of highly invasive and metastazising cancers where uPA and uPAR have been found to be consistently present at the invasive foci of the tumor [Dano et al., *Proteolysis and Protein Turnover*, eds. Barret+Bond, Portlan Press, 1994, London] (e.g. breast, lung, colon, ovarian cancers). In patients with breast cancer and non-small cell lung cancer increased levels of uPAR in plasma have been detected. Therefore, the amount of soluble uPAR appears to reflect the degree of proteolysis in the tumor and this might be closely related to patient prognosis. Both uPA and uPAR levels in tumor tissue are prognostic factors in many types of cancers.

In addition to cancer, other diseases mediated by cell-surface activity of uPA are addressed by uPAR antagonists. Inhibitors of plasmin generation by receptor bound uPA therefore have mechanism-based tumoristatic, anti-invasive, anti-metastatic, anti-angiogenic, anti-arthritic, anti-inflammatory, anti-osteoporotic, anti-retinopathic and contraceptive activities.

We have now discovered that derivatives of 2-alkylidene hydroxycoumaranones wherein the hydroxy group is substituted by a nitrogen-containing residue have a significant activity of inhibition of the uPA/uPAR system functions by antagonizing the uPA receptor. These compounds possess antitumor and antimetastatic activity.

Some 6- and 4-piperidinoalkyloxy-2-alkylidenecoumaranones are already described in EP 0 088 986 as antihistaminic agents and as inhibitors of the anaphylactic shock. No antitumor or antimetastatic activities have been reported to date.

BRIEF DESCRIPTION OF THE INVENTION

In one aspect, the invention relates to a compound of formula I

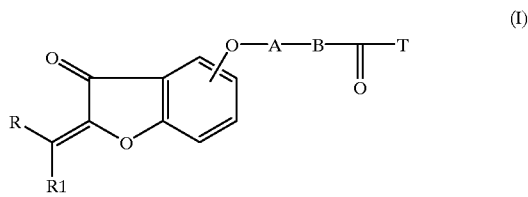

wherein:

R and $R^1$ are independently hydrogen, $(C_1-C_6)$alkyl, styryl or $(C_3-C_6)$cycloalkyl or, taken together with the carbon to which they are linked, form a $(C_3-C_6)$ cycloalkyl group;

A is:
—CH$_2$C≡CCH$_2$—,

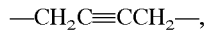

or —(CH$_2$)$_q$—NH—(CH$_2$)$_q$—,
wherein q is an integer from 2 to 3

B is:

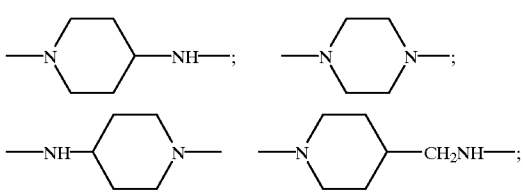

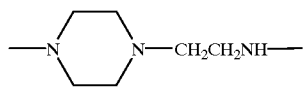

T is —CH$_2$—C≡CH, —C≡CH, —(CH$_2$)$_p$—R$_3$, —CH=CH—R$_3$,

—CH$_2$—NHCO—R$_3$, —(CH$_2$)$_p$—O—R$_3$, or —CH(NH$_2$)—CH$_2$R$_3$, wherein p is 0 or an integer from 1 to 4, and R$_3$ is phenyl, naphthyl, biphenyl, each being unsubstituted or substituted by one or more groups selected from chlorine, bromine, iodine, fluorine, (C$_1$-C$_6$)alkyl, cyano, nitro, mono- or polyfluoroalkyl, —SO$_2$(C$_1$-C$_4$)alkyl, —SO$_2$NH$_2$, —SO$_2$NH(C$_1$-C$_4$)alkyl, —SO$_2$N[(C$_1$-C$_4$)alkyl]$_2$, —CONH$_2$, —CONH(C$_1$-C$_4$)alkyl, hydroxy, amino, carboxy, (C$_1$-C$_4$)alkoxy, (C$_1$-C$_4$) mono- or di-alkyl amino, (C$_1$-C$_4$)alkoxycarbonyl, mercapto, (C$_1$-C$_4$)alkylthio or R$_3$ is a 5- or 6-membered unsubstituted or substituted heterocycle which contains 1 or 2 heteroatoms selected from oxygen, sulfur or nitrogen and which is or is not benzocondensed, wherein the substituents are one or more groups selected from chlorine, bromine, iodine, fluorine, (C$_1$-C$_6$)alkyl, cyano, nitro, mono- or polyfluoroalkyl, —SO$_2$(C$_1$-C$_4$)alkyl, —SO$_2$NH$_2$, —SO$_2$NH(C$_1$-C$_4$)alkyl, —SO$_2$N[(C$_1$-C$_4$)alkyl]$_2$, —CONH$_2$, —CONH(C$_1$-C$_4$)alkyl, hydroxy, amino, carboxy, (C$_1$-C$_4$)alkoxy, (C$_1$-C$_4$)mono- or di-alkyl amino, (C$_1$-C$_4$)alkoxycarbonyl, mercapto, (C$_1$-C$_4$)alkylthio, or an enantiomer, diastereoisomer, racemate or mixture thereof, or a pharmaceutically acceptable salt thereof.

In a preferred aspect, the invention relates to a compound of formula IA (IA)

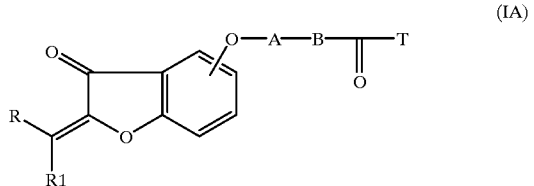

wherein:

R and R$^1$ are independently hydrogen, (C$_1$-C$_6$)alkyl, styryl or (C$_3$-C$_6$)cycloalkyl or, taken together with the carbon to which they are linked, form a (C$_3$-C$_6$) cycloalkyl group;

A is:

—CH$_2$C≡CCH$_2$—,

B is:

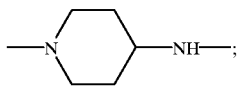

T is —(CH$_2$)$_p$—R$_3$, wherein p is 0, and

R$_3$ is phenyl which is unsubstituted or substituted by one or more groups selected from chlorine, bromine, iodine, fluorine, mono- or polyfluoroalkyl, —SO$_2$NH$_2$, or an enantiomer, diastereoisomer, racemate or mixture thereof, or a pharmaceutically acceptable salt thereof.

The compounds of formula I, their enantiomers, diastereoisomers, racemates, mixtures thereof, and salts thereof with pharmaceutically acceptable acids and bases are uPA-uPAR antagonists and have antitumor and antimetastatic activity.

In a preferred embodiment of compounds of formula IA, R and R$^1$ are independently (C$_1$-C$_6$)alkyl, or styryl.

In a more preferred embodiment of compounds of formula IA, R and R$^1$ are independently (C$_1$-C$_6$)alkyl and A is —CH$_2$C≡CCH$_2$—,

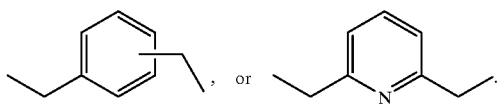

In another preferred embodiment of compounds of formula IA, R and R$^1$ are independently styryl and A is

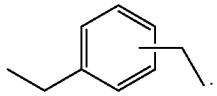

DETAILED DESCRIPTION OF THE INVENTION

The present invention relates to compounds of the formula (I):

(I)

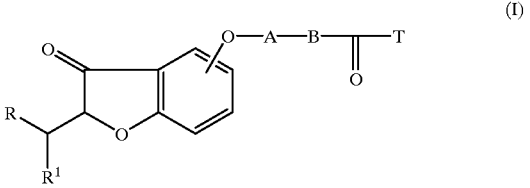

wherein:

R and R$^1$ are independently hydrogen, (C$_1$-C$_6$)alkyl, styryl and (C$_3$-C$_6$)cycloalkyl or, taken together with the carbon to which they are linked, form a (C$_3$-C$_6$) cycloalkyl group;

A is:
—CH$_2$C≡CCH$_2$—,

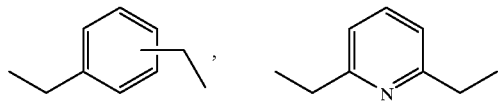

or —(CH$_2$)$_q$—NH—(CH$_2$)$_q$—,
wherein q is an integer from 2 to 3

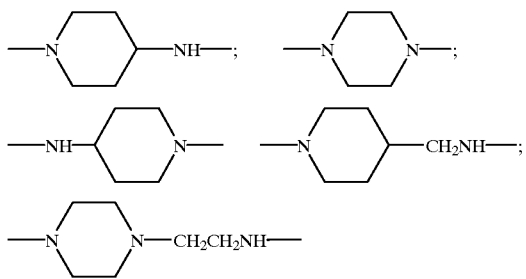

B is:
T is —CH$_2$—C≡CH, —C≡CH, —(CH$_2$)$_p$—R$_3$, —CH=CH—R$_3$, —CH$_2$—NHCO—R$_3$, —(CH$_2$)$_p$—O—R$_3$, or —CH(NH$_2$)—CH$_2$R$_3$, wherein which p is 0 or an integer from 1 to 4, and R$_3$ is phenyl, naphthyl, or biphenyl, which are unsubstituted or substituted by one or more groups selected from chlorine, bromine, iodine, fluorine, (C$_1$–C$_6$)alkyl, cyano, nitro, mono- or polyfluoroalkyl, —SO$_2$(C$_1$–C$_4$)alkyl, —SO$_2$NH$_2$, —SO$_2$NH(C$_1$–C$_4$)alkyl, —SO$_2$N[(C$_1$–C$_4$)alkyl]$_2$, —CONH$_2$, —CONH(C$_1$–C$_4$)alkyl, hydroxy, amino, carboxy, (C$_1$–C$_4$)alkoxy, (C$_1$–C$_4$) mono- or di-alkyl amino, (C$_1$–C$_4$)alkoxycarbonyl, mercapto, (C$_1$–C$_4$)alkylthio or R$_3$ is a 5- or 6-membered unsubstituted or substituted heterocycle which contains 1 or 2 heteroatoms selected from oxygen, sulfur or nitrogen, which is or is not benzocondensed, wherein the substituents are one or more groups selected from chlorine, bromine, iodine, fluorine, (C$_1$–C$_6$)alkyl, cyano, nitro, mono- or polyfluoroalkyl, —SO$_2$(C$_1$–C$_4$)alkyl, —SO$_2$NH$_2$, —SO$_2$NH(C$_1$–C$_4$)alkyl, —SO$_2$N[(C$_1$–C$_4$)alkyl]$_2$, —CONH$_2$, —CONH(C$_1$–C$_4$)alkyl, hydroxy, amino, carboxy, (C$_1$–C$_4$)alkoxy, (C$_1$–C$_4$)mono- or di-alkyl amino, (C$_1$–C$_4$)alkoxycarbonyl, mercapto, (C$_1$–C$_4$) alkylthio.

The enantiomers of the compounds of formula (I), their diastereoisomers, racemates and mixtures thereof are also included in the present invention, as well as the salts of the compounds of formula (I) with pharmaceutically acceptable acids or bases.

The 5- and 6-membered heterocycles which may or may not be benzocondensed referred to above are preferably selected from thiophene, pyridine, imidazole, furane, quinoline, isoquinoline, indole, benzothiazole and benzimidazole. The term "benzocondensed" means that the heterocycle has two carbon atoms in common with a phenyl ring. Examples of benzocondensed 5- and 6-membered heterocycles are imidazole, quinoline, isoquinoline, indole, benzothiazole, and benzimidazole.

Preferred compounds of formula (I) are those in which A is a butynylidene or xylylene group and in which B is a piperazine or a piperidyl-NH-group, T is an unsubstituted or substituted phenyl ring and R and R$^1$ are CH$_3$. Particularly preferred compounds of formula (I) are those in which A is a butynylidene or xylylene group and in which B is a piperidine-NH-group, T is a phenyl ring substituted one or two times by fluoro, bromo, chloro or SO$_2$NH$_2$ and R and R$^1$ are methyl, especially when the coumaranone is substituted in the 4 position.

The most preferred compounds are:

4-{4-[4-(3-aminosulfonyl-4-chlorobenzamido)piperidino] but-2-ynoxy}-2-isopropylidenecoumaran-3-one 4-{3-[4-(4-fluorobenzamido)piperidinomethyl] phenylmethoxy}-2-isopropylidenecoumaran-3-one 4-{3-[4-(4-bromobenzamido)piperidinomethyl] phenylmethoxy}-2-isopropylidenecoumaran-3-one 4-{3-[4-(3-aminosulfonyl-4-chlorobenzamido) piperidinomethyl]phenylmethoxy}-2-isopropylidenecoumaran-3-one 4-{3-[4-(3,4-dichlorobenzamido)piperidinomethyl] phenylmethoxy}-2-isopropylidenecoumaran-3-one 4-{6-[4-(4-fluorobenzamido)piperidinomethyl]pyridinyl-2-methoxy}-2-isopropylidenecoumaran-3-one 4-{2-{2-[4-(4-fluorobenzamido)piperidino] ethylamino}ethoxy}-2-isopropylidenecoumaran-3-one 4-{2-{2-[4-(4-bromobenzamido)piperidino] ethylamino}ethoxy}-2-isopropylidenecoumaran-3-one 4-{2-{2-[4-(3,4-dichlorobenzamido)piperidino] ethylamino}ethoxy}-2-isopropylidenecoumaran-3-one 4-{2-{2-[4-(3-aminosulfonyl-4-chlorobenzamido) piperidino]ethylamino}ethoxy}-2-isopropylidenecoumaran-3-one Another object of the present invention are pharmaceutical compositions containing a pharmacologically effective amount of one or more compounds of formula (I) in admixture with pharmaceutically acceptable excipients and/or diluents.

PREPARATION OF THE COMPOUNDS OF THE INVENTION

The compounds of formula (I) and their pharmaceutically acceptable salts can be prepared according to the two-step process described in EP 088 986, which is herein incorporated by reference, which comprises reacting a compound of formula (II):

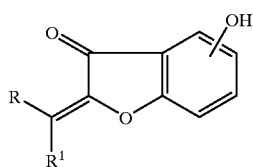

(II)

in which R and R$^1$ have the above meanings, with a compound of formula (III):

L—A—L'            (III)

in which A has the above meanings and L, L' are leaving groups, which can be the same or different, and are preferably selected from chlorine, bromine, iodine, mesyl or tosyl groups, and a compound of formula (IV):

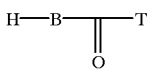

in which B and T have the above meanings, said compounds being reacted in two possible ways:

(i) reaction of a compound of formula (II) with a compound of formula (III), followed by reaction of the so obtained product with a compound of formula (IV), or alternatively (ii) reaction of a compound of formula (IV) with a compound of formula (III), followed by reaction of the so obtained product with a compound of formula (II).

In both cases, the intermediate product of the first synthesis step is preferentially isolated before submitting it to the second reaction. In such a process in general the oxygen-alkylation is performed under strongly basic conditions, preferably by means of an alkoxide of alkaline metal such as sodium ethoxide or isopropoxide or potassium carbonate in a suitable solvent, preferably a ($C_1$–$C_4$)alkyl alcohol or dimethylformamide, and at temperatures ranging from 20° C. to the boiling temperature of the solvent.

The nitrogen-alkylation is instead performed at milder conditions, in the presence of a base such as an organic base, preferably a trialkylamine, or an inorganic base, preferably a carbonate of an alkaline or alkaline-earth metal, at temperatures ranging from room temperature to 50° C.

The compounds of formula (II) are obtained from the compounds of formula (II'):

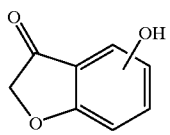

by reaction with an aldehyde or ketone of formula R—CO—$R^1$, in which R and $R^1$ are as above defined, in the presence of a base, preferably a hydroxide of an alkaline metal, in a solvent and at temperatures up to 100° C. A preferred reaction employs potassium hydroxide at reflux in ethanol.

The compounds of formula (II') are known and are described in J. Am. Chem. Soc., 61, 2328 (1939), which is herein incorporated by reference.

The compounds of formula (III) are commercial products or can easily be prepared starting from commercial products according to usual reactions such as halogenation of alcohols or their conversion into mesyl and tosyl derivatives.

The compounds of formula (IV) can be prepared starting from a suitably mono-protected diamine of formula P—B—H, in which P is for example a benzyl or tert-butoxycarbonyl group, by acylation with a compound of formula (IV'):

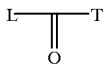

in which L and T have the above meanings, preferably in the presence of a base and of an inert solvent at temperatures ranging from 0° C. to 50° C.

The mono-protected diamines of formula P—B—H and the compounds of formula (IV') are known commercial products or can be prepared therefrom according to known methods.

BIOLOGICAL ACTIVITY OF THE COMPOUNDS OF THE INVENTION

The compounds of the invention were tested (ELISA test) as inhibitors of human urokinase (uPA) binding to its specific receptor uPAR mAk (BIO-R4), according to the procedure described in Biol. Chem. Hoppe-Seyler, 376, 587–94 (1995) by Rettenberger et al. The assays are performed in Microtiterplates (96 wells). The following solutions are used:

washing buffer: PBS-buffer (without $Mg^{2+}$ and $Ca^{2+}$)+ 0.05% Tween 20;

incubation buffer (IP): 1% skimmed milk powder in PBS-buffer (without $Mg^{2+}$ and $Ca^{2+}$);

BIO-R4 solution: 50 ng/well (0.5 µg/ml; 100 µl/well) in IP;

uPAR solution: 3 ng/well (30 ng/ml; 100 µl/well) in PBS-buffer (without $Mg^{2+}$ and $Ca^{2+}$);

blocking solution: 1% skimmed milk powder in washing buffer (dissolved at 37° C.);

uPA solution: 0.25 ng/well (5 ng/ml; 50 µl/well) in IP.

Detection Solutions (per microtiterplate):

(1) 6 ml (100 mM Tris-Cl pH 7.2+0.15% Tween 80)+1.5 ml (10 µg) plasminogen in aqua bidest;

(2) 6 ml (100 mM Tris-Cl pH 7.2+0.15% Tween 80)+1.5 ml (7.5 mg) chromozyme PL in aqua bidest.

The detection solution must be continuously stirred. Testing substances: the testing substances are dissolved in DMSO. They are used in the test system with a highest concentration of 100 µg/ml. The solutions are prepared using PBS.

Three controls are performed:

a) positive control: using 2% DMSO in PBS;

b) negative control: assay without receptor;

c) inhibition control:

1) inhibition ($IC_{95}$ at 0.25 mg/ml) with dextranesulfate (MW=500.000);

2) inhibition ($IC_{90}$ at 1 µg/ml) with inactivated uPA (175 µg/ml).

Incubation is done as follows:

Each well is incubated by 100 µl of BIO-R4 (c=0.5 µg/ml) for 1 hour at room temperature under shaking. After washing three times with the washing buffer, each well is incubated for 1 hour (37° C.) with 200 µl/well blocking solution. After triple washing each well is incubated for 1 hour at room temperature under shaking with 100 µl/well uPAR (c=30 ng/ml), then the wells are washed again three times with the washing buffer. The testing substance solution and the control solution, respectively, are added (50 µl/well) and are incubated for 30 minutes at room temperature under shaking. An additional 50 µl of uPA solution (c=2.5 ng/ml) are added. After 1 hour at room temperature a triple washing is performed.

For detection, the following procedure is used:

Incubation with 50 µl each of detection solution (1) and (2) at room temperature. After 20 minutes a yellow colour will be visible (the positive control reads an extinction of 1 after 45–60 minutes). The detection is performed at 405 nm (reference is 490 nm) using a Dynatech MR 7000 ELISA reader. To obtain the percentage of inhibition the following formula is used (E stands for extinction):

$$\% \text{ Inhibition}=100-100\times[E_{test}-E_{neg.control}/E_{pos.control}-E_{neg.control}]$$

The data for a representative compound of the invention are reported in Table I.

TABLE I

BIO-R4 Assay - Inhibition of uPA binding to the specific uPAR receptor (BIO-R4) expressed as $IC_{50}$ ($\mu M$)

| structure | example | $IC_{50}$ ($\mu M$) |
|---|---|---|
| 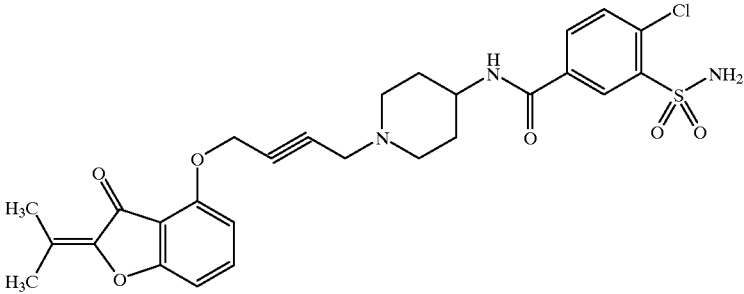 | 4 | 1.79 |
| 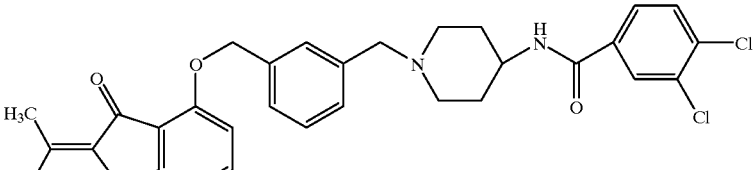 | 11 | 1.41 |

The invention concerns pharmaceutical agents containing one or more compounds of formula (I).

In order to produce pharmaceutical agents, the compounds of formula (I) are mixed in a known manner with suitable pharmaceutical carrier substances, aromatics, flavouring and dyes and are formed for example into tablets or coated tablets or they are suspended or dissolved in water or an oil such as e.g. olive oil with addition of appropriate auxiliary substances.

The compounds of formula (I) can be administered orally or parenterally in a liquid or solid form. Water is preferably used as the medium which contains the stabilizing agents, solubilizers and/or buffers which are usually used for injection solutions. Such additives are for example tartrate or borate buffers, ethanol, dimethylsulfoxide, complexing agents (such as ethylenediaminetetraacetic acid), high molecular polymers (such as liquid polyethylene oxide) for the regulation of the viscosity or polyethylene derivatives of sorbitol anhydrides.

Solid carrier substances are e.g. starch, lactose, mannitol, methylcellulose, talcum, highly dispersed silicic acid, higher molecular fatty acids (such as stearic acid), gelatin, agar—agar, calcium phosphate, magnesium stearate, animal and vegetable fats or solid high molecular polymers (such as polyethylene glycols). Suitable formulations for the oral route can if desired contain flavourings and sweeteners.

The administered dose depends on the age, the health and the weight of the patient, the extent of the disease, the type of treatments which are possibly being carried out concurrently, the frequency of the treatment and the type of the desired effect. The daily dose of the active compound is usually 0.1 to 50 mg/kg body weight. Normally 0.5 to 40 and preferably 1 to 20 mg/kg/day in one or several applications per day are effective in order to obtain the desired results.

The invention is further illustrated by the following examples:

PREPARATION 1

4-(4-chloro-but-2-ynoxy)-2-isopropylidenecoumaran-3-one

A mixture of 5.0 g 4-hydroxy-2-isopropylidenecoumaran-3-one, 4.6 g potassium carbonate, 3.3 ml 1,4-dichloro-but-2-yne and 100 ml dimethylformamide is warmed to 50° C. for 3 hours, then evaporated, mixed with water and extracted with dichloromethane. After evaporation of the extract, the residue (9.2 g) is purified by silica gel chromatography (eluent isohexane/ethyl acetate 9:1) to give 2.2 g of the desired intermediate.

EXAMPLE 1

4-{4-[4-(4-fluorobenzamido)piperidino]but-2-ynoxyl}-2-isopropylidenecoumaran-3-one A mixture of 690 mg 4-(4-chloro-but-2-ynoxy)-2-isopropylidenecoumaran-3-one (preparation 1), 350 mg potassium carbonate, 560 mg 4-(4-fluorobenzamido) piperidine and 15 ml dimethylformamide is warmed to 60° C. for 3 hours, then evaporated, mixed with water and extracted with dichloromethane. After evaporation of the extract, the residue (1.2 g) is purified by silica gel chromatography (eluent isohexane/ethyl acetate 1:3) to give 840 mg (73%) of the desired compound, m.p. 160–161° C.

EXAMPLE 2

4-{4-[4-(4-trifluoromethylbenzamido)piperidino]but-2-ynoxy}-2-isopropylidenecoumaran-3-one Analogously to example 1, the title compound is obtained from the reaction of 4-(4-chloro-but-2-ynoxy)-2-isopropylidenecoumaran-3-one (preparation 1) with 4-(4-trifluoromethylbenzamido)piperidine in 42% yield, m.p. 196–197° C.

EXAMPLE 3

4-{4-[4-(4-bromobenzamido)piperidino]but-2-ynoxy}-2-isopropylidenecoumaran-3-one Analogously to example 1, the title compound is obtained from the reaction of 4-(4-chloro-but-2-ynoxy)-2-isopropylidenecoumaran-3-one (preparation 1) with 4-(4-bromobenzamido)piperidine in 57% yield, m.p. 217–219° C.

EXAMPLE 4

4-{4-[4-(3-aminosulfonyl-4-chlorobenzamido)
piperidino]but-2-ynoxyl}-2-
isopropylidenecoumaran-3-one Analogously to example 1, the title compound is obtained from the reaction of 4-(4-chloro-but-2-ynoxy)-2-isopropylidenecoumaran-3-one (preparation 1) with 4-(3-aminosulfonyl-4-chlorobenzamido)piperidine in 45% yield, m.p. 127–129° C.

EXAMPLE 5

4-{4-[4-(3,4-dichlorobenzamido)piperidino]but-2-
ynoxy}-2-isopropylidenecoumaran-3-one Analogously to example 1, the title compound is obtained from the reaction of 4-(4-chloro-but-2-ynoxy)-2-isopropylidenecoumaran-3-one (preparation 1) with 4-(3,4-dichlorobenzamido)piperidine in 81% yield, m.p. 208–210° C.

PREPARATION 2

4-(4-chloromethyl-phenylmethoxy)-2-
isopropylidenecoumaran-3-one 2.8 g Potassium carbonate is added over 3 hours to a mixture of 3.8 g 4-hydroxy-2-isopropylidenecoumaran-3-one, 3.5 g 1,4-bis-(chloromethyl)benzene and 150 ml butanone at 70–75° C. The mixture is refluxed for 16 hours, then filtered, the filtrate evaporated and the residue purified by silica gel chromatography (eluent isohexane/ethyl acetate 3:1) to give 1.3 g of the desired intermediate.

EXAMPLE 6

4-{4-[4-(4-fluorobenzamido)piperidinomethyl]
phenylmethoxyl}-2-isopropylidenecoumaran-3-one A mixture of 570 mg 4-(4-chloromethyl-phenylmethoxy)-2-isopropylidenecoumaran-3-one (preparation 2), 240 mg potassium carbonate, 400 mg 4-(4-fluorobenzamido)piperidine and 15 ml dimethylformamide is warmed to 60° C. for 3 hours, then evaporated, mixed with water and extracted with ethyl acetate. After evaporation of the extract, the residue (0.6 g) is purified by silica gel chromatography (eluent ethyl acetate) to give 180 mg (19%) of the desired compound, m.p. 205–208° C.

EXAMPLE 7

4-{4-[4-(4-trifluoromethylbenzamido)
piperidinomethyl]phenylmethoxy}-2-
isopropylidenecoumaran-3-one Analogously to example 6, the title compound is obtained from the reaction of 4-(4-chloromethyl-phenylmethoxy)-2-isopropylidenecoumaran-3-one (preparation 2) with 4-(4-trifluoromethylbenzamido)piperidine in 13% yield, m.p. 191–193° C.

PREPARATION 3

4-(3-chloromethyl-phenylmethoxy)-2-
isopropylidenecoumaran-3-one

Analogously to preparation 2, the title compound is obtained from the reaction of 4-hydroxy-2-isopropylidenecoumaran-3-one with 1,3-bis-(chloromethyl)benzene in 18% yield.

EXAMPLE 8

4-{3-[4-(4-fluorobenzamido)piperidinomethyl]
phenylmethoxyl}-2-isopropylidenecoumaran-3-one Analogously to example 6, the title compound is obtained from the reaction of 4-(3-chloromethyl-phenylmethoxy)-2-isopropylidenecoumaran-3-one (preparation 3) with 4-(4-fluorobenzamido)piperidine in 27% yield, m.p. 100–105° C. (amorphous).

EXAMPLE 9

4-{3-[4-(4-bromobenzamido)piperidinomethyl]
phenylmethoxy}-2-isopropylidenecoumaran-3-one Analogously to example 6, the title compound is obtained from the reaction of 4-(3-chloromethyl-phenylmethoxy)-2-isopropylidenecoumaran-3-one (preparation 3) with 4-(4-bromobenzamido)piperidine in 37% yield, m.p. 181–183° C.

EXAMPLE 10

4-{3-[4-(3-aminosulfonyl-4-chlorobenzamido)
piperidinomethyl]phenylmethoxyl}-2-
isopropylidenecoumaran-3-one Analogously to example 6, the title compound is obtained from the reaction of 4-(3-chloromethyl-phenylmethoxy)-2-isopropylidenecoumaran-3-one (preparation 3) with 4-(3-aminosulfonyl-4-chlorobenzamido)piperidine in 41% yield, m.p. 78–80° C. (amorphous).

EXAMPLE 11

4-{3-[4-(3,4-dichlorobenzamido)piperidinomethyl]
phenylmethoxy}-2-isopropylidenecoumaran-3-one Analogously to example 6, the title compound is obtained from the reaction of 4-(3-chloromethyl-phenylmethoxy)-2-isopropylidenecoumaran-3-one (preparation 3) with 4-(3,4-dichlorobenzamido)piperidine in 71% yield, m.p. 173–175° C.

PREPARATION 4

4-(2-chloromethyl-phenylmethoxy)-2-
isopropylidenecoumaran-3-one

Analogously to preparation 2, the title compound is obtained from the reaction of 4-hydroxy-2-isopropylidenecoumaran-3-one with 1,2-bis-(chloromethyl)benzene in 11% yield.

EXAMPLE 12

4-{2-[4-(4-fluorobenzamido)piperidinomethyl]
phenylmethoxy}-2-isopropylidenecoumaran-3-one Analogously to example 6, the title compound is obtained from the reaction of 4-(2-chloromethyl-phenylmethoxy)-2-isopropylidenecoumaran-3-one (preparation 4) with 4-(4-fluorobenzamido)piperidine in 84% yield, m.p. 98–99° C.

PREPARATION 5

4-(6-chloromethyl-pyridinyl-2-methoxy)-2-
isopropylidenecoumaran-3-one

Analogously to preparation 2, the title compound is obtained from the reaction of 4-hydroxy-2- isopropylidenecoumaran-3-one with 2,6-bis-(chloromethyl) pyridine in 34% yield.

EXAMPLE 13

4-{6-[4-(4-fluorobenzamido)piperidinomethyl] pyridinyl-2-methoxy}-2-isopropylidenecoumaran-3-one Analogously to example 6, the title compound is obtained from the reaction of 4-(6-chloromethyl-pyridinyl-2-methoxy)-2-isopropylidenecoumaran-3-one (preparation 5) with 4-(4-fluorobenzamido)piperidine in 29% yield, m.p. 193–195° C.

PREPARATION 6

6-(3-chloromethyl-phenylmethoxy)-2-cinnamylidenecoumaran-3-one

Analogously to preparation 2, the title compound is obtained from the reaction of 6-hydroxy-2-cinnamylidenecoumaran-3-one with 1,3-bis-(chloromethyl) benzene in 28% yield.

EXAMPLE 14

6-{3-[4-(4-fluorobenzamido)piperidinomethyl] phenylmethoxy}-2-cinnamylidenecoumaran-3-one A mixture of 520 mg 6-(3-chloromethyl-phenylmethoxy)-2-cinnamylidenecoumaran-3-one (preparation 6), 150 mg sodium hydrogencarbonate, 330 mg 4-(4-fluorobenzamido) piperidine and 15 ml dimethylformamide is warmed to 60° C. for 3 hours, then evaporated, mixed with water and extracted with ethyl acetate. After evaporation of the extract, the residue is purified by silica gel chromatography (eluent ethyl acetate) to give 500 mg (65%) of the desired compound, m.p. 126–128° C.

EXAMPLE 15

6-{3-[4-(4-bromobenzamido)piperidinomethyl] phenylmethoxyl}-2-cinnamylidenecoumaran-3-one Analogously to example 14, the title compound is obtained from the reaction of 6-(3-chloromethyl-phenylmethoxy)-2-cinnamylidenecoumaran-3-one (preparation 6) with 4-(4-bromobenzamido)piperidine in 66% yield, m.p. 199–201° C.

EXAMPLE 16

6-{3-[4-(3,4-dichlorobenzamido)piperidinomethyl] phenylmethoxy}-2-cinnamylidenecoumaran-3-one Analogously to example 14, the title compound is obtained from the reaction of 6-(3-chloromethyl-phenylmethoxy)-2-cinnamylidenecoumaran-3-one (preparation 6) with 4-(3,4-dichlorobenzamido)piperidine in 60% yield, m.p. 184–186° C.

What is claimed is:

1. A compound of formula I

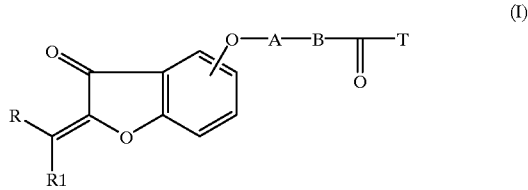

wherein:

R and $R^1$ are independently hydrogen, $(C_1$–$C_6)$alkyl, styryl or $(C_3$–$C_6)$cycloalkyl or, taken together with the carbon to which they are linked, form a $(C_3$–$C_6)$ cycloalkyl group;

A is:

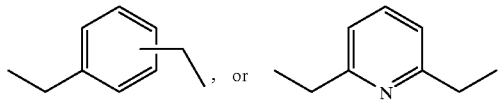

B is:

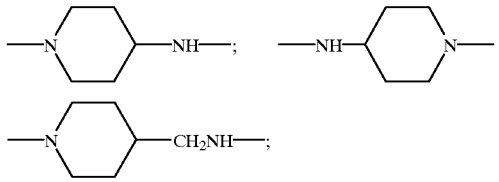

T is —$CH_2$—C≡CH, —C≡CH, —$(CH_2)_p$—$R_3$, —CH=CH—$R_3$, —$CH_2$—NHCO—$R_3$, —$(CH_2)_p$—O—$R_3$, or —$CH(NH_2)$—$CH_2R_3$, wherein p is 0 or an integer from 1 to 4, and $R_3$ is phenyl, naphthyl, biphenyl, each being unsubstituted or substituted by one or more groups selected from chlorine, bromine, iodine, fluorine, $(C_1$–$C_6)$alkyl, cyano, nitro, mono- or polyfluoroalkyl, —$SO_2(C_1$–$C_4)$alkyl, —$SO_2NH_2$, —$SO_2NH(C_1$–$C_4)$alkyl, —$SO_2N[(C_1$–$C_4)$alkyl]$_2$, —$CONH_2$, —$CONH(C_1$–$C_4)$alkyl, hydroxy, amino, carboxy, $(C_1$–$C_4)$alkoxy, $(C_1$–$C_4)$ mono- or di-alkyl amino, $(C_1$–$C_4)$alkoxycarbonyl, mercapto, $(C_1$–$C_4)$alkylthio or $R_3$ is a 5- or 6-membered unsubstituted or substituted heterocycle which contains 1 or 2 heteroatoms selected from oxygen, sulfur or nitrogen and which is or is not benzocondensed, wherein the substituents are one or more groups selected from chlorine, bromine, iodine, fluorine, $(C_1$–$C_6)$alkyl, cyano, nitro, mono- or polyfluoroalkyl, —$SO_2(C_1$–$C_4)$alkyl, —$SO_2NH_2$, —$SO_2NH(C_1$–$C_4)$alkyl, —$SO_2N[(C_1$–$C_4)$alkyl]$_2$, —$CONH_2$, —$CONH(C_1$–$C_4)$alkyl, hydroxy, amino, carboxy, $(C_1$–$C_4)$alkoxy, $(C_1$–$C_4)$mono- or di-alkyl amino, $(C_1$–$C_4)$alkoxycarbonyl, mercapto, $(C_1$–$C_4)$ alkylthio, or an enantiomer, diastereoisomer, racemate or mixture thereof, or a pharmaceutically acceptable salt thereof.

2. A compound of formula I according to claim 1, of formula IA

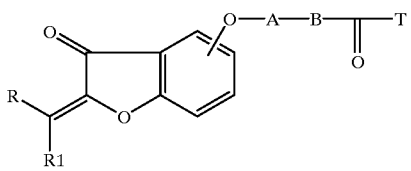
(IA)

wherein:

R and $R^1$ are independently hydrogen, $(C_1-C_6)$alkyl, styryl or $(C_3-C_6)$cycloalkyl or, taken together with the carbon to which they are linked, form a $(C_3-C_6)$ cycloalkyl group;

A is:

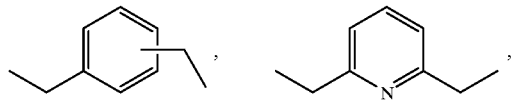

B is:

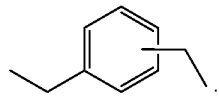

T is —$(CH_2)_p$—$R_3$, wherein p is 0, and $R_3$ is phenyl which is unsubstituted or substituted by one or more groups selected from chlorine, bromine, iodine, fluorine, mono- or polyfluoroalkyl, —$SO_2NH_2$, or an enantiomer, diastereoisomer, racemate or mixture thereof, or a pharmaceutically acceptable salt thereof.

3. A compound of formula IA according to claim 1, wherein A is

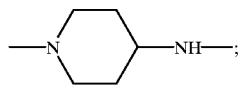

4. A compound of formula IA according to claim 3, wherein R and $R^1$ are independently hydrogen, $(C_1-C_6)$ alkyl, or styryl.

5. A compound of formula IA according to claim 4, wherein R and $R^1$ are independently $(C_1-C_6)$alkyl.

6. A compound of formula I according to claim 1, wherein the compound is 4-{4-[4-(4-fluorobenzamido) piperidinomethyl]phenylmethoxy}-2-isopropylidenecoumaran-3-one.

7. A compound of formula I according to claim 1, wherein the compound is 4-{4-[4-(4-trifluoromethylbenzamido) piperidinomethyl]phenylmethoxy}-2-isopropylidenecoumaran-3-one.

8. A compound of formula I according to claim 1, wherein the compound is 4-{3-[4-(4-fluorobenzamido) piperidinomethyl]phenylmethoxy}-2-isopropylidenecoumaran-3-one.

9. A compound of formula I according to claim 1, wherein the compound is 4-{3-[4-(4-bromobenzamido) piperidinomethyl]phenylmethoxy}-2-isopropylidenecoumaran-3-one.

10. A compound of formula I according to claim 1, wherein the compound is 4-{3-[4-(3-aminosulfonyl-4-chlorobenzamido)piperidinomethyl]phenylmethoxy}-2-isopropylidenecoumaran-3-one.

11. A compound of formula I according to claim 1, wherein the compound is 4-{3-[4-(3,4-dichlorobenzamido) piperidinomethyl]phenylmethoxy}-2-isopropylidenecoumaran-3 -one.

12. A compound of formula I according to claim 1, wherein the compound is 4-{2-[4-(4-fluorobenzamido) piperidinomethyl]phenylmethoxy}-2-isopropylidenecoumaran-3-one.

13. A compound of formula IA according to claim 4, wherein R is styryl and $R^1$ is hydrogen.

14. A compound of formula I according to claim 1, wherein the compound is 6-{3-[4-(4-fluorobenzamido) piperidinomethyl]phenylmethoxy}-2-cinnamylidenecoumaran-3-one.

15. A compound of formula I according to claim 1, wherein the compound is 6-{3-[4-(4-bromobenzamido) piperidinomethyl]phenylmethoxy}-2-cinnamylidenecoumaran-3-one.

16. A compound of formula IA according to claim 1, wherein the compound is 6-{3-[4-(3,4-dichlorobenzamido) piperidinomethyl]phenylmethoxy}-2-cinnamylidenecoumaran-3-one.

17. A compound of formula IA according to claim 1, wherein A is

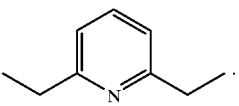

18. A compound of formula I according to claim 1, wherein the compound is 4-{6-[4-(4-fluorobenzamido) piperidinomethyl]pyridinyl-2-methoxy}-2-isopropylidenecoumaran-3-one.

* * * * *